United States Patent [19]

Kuna et al.

[11] Patent Number: 5,474,983
[45] Date of Patent: Dec. 12, 1995

[54] METHOD OF INHIBITING PRO-INFLAMMATORY MEDIATOR RELEASE FROM BASOPHILS AND MAST CELLS

[75] Inventors: Piotr Kuna, Port Jefferson; Allen P. Kaplan, St. James, both of N.Y.

[73] Assignee: The Research Foundation of State University of New York, Stony Brook, N.Y.

[21] Appl. No.: 31,772

[22] Filed: Mar. 15, 1993

[51] Int. Cl.⁶ .................................................. A61K 38/19
[52] U.S. Cl. ...................................... 514/12; 514/21
[58] Field of Search ................................. 514/12, 21

[56] References Cited

FOREIGN PATENT DOCUMENTS 9201465  2/1992  WIPO.

OTHER PUBLICATIONS

Goodman & Gilman "The Pharmacological Basis of Therapeutics" pp. 620, 623–624 (1985).
Alam et al., Clin. Res., vol. 40(2), p. 229A, 1992.
Alam et al., The FASEB J., vol. 6, p. A2005, 1992.
Alam et al., Am. J. Respir. Cell Mol. Biol., vol. 7, pp. 427–433, 1992.
Wolpe et al., The FASEB J., vol. 3, pp. 2565–2573, 1989.
Oppenheim et al., Annu. Rev. Immunol., vol. 9, pp. 617–648, 1991.
Averill et al., Am. Rev. Respir. Dis., 145:571–576 (1992).
Brindley et al., J. Clin. Invest., 72:1218–1223 (1983).
Fisher et al., J. Allergy Clin. Immunol., 91(1):Abstracts 225, No. 339 (1992).
Fisher et al., J. Allergy Clin. Immunol., 89(1):Abstracts 165, No. 81 (1992).
Goetzl et al., J. Exp. Med., 158:731–737 (1983).
Irvin, J. Allergy Clin. Immunol., 90(3):521–533 (1992).
Knauer et al., Int. Archs. Allergy appl. Immun., 74:29–35 (1984).
Kuna et al., J. Allergy Clin. Immunol., 91: Abstracts 314, No. 695 (1993).
Kuna et al., J. Immunol., 149:636 (1992).
Kuna et al., J. Immunol. 147:1920–1924 (1991).
Kuna et al., J. Immunol. 150:1932–1943 (Mar., 1993).
Kuna et al., J. Exp. Med., 175:489 (1992).
McFadden, et al., Chap. 257 "Asthma," Harrison's Principles of Internal Medicine, 1349–1354 (McGraw-Hill, Inc. 1977).
Metzger et al., J. Allergy Clin. Immunol., 91(1):Abstracts 163, No. 89 (1993).
Alam et al., J. Clin. Invest., 89:723 (1992).
Alam et al., J. Clin. Invest., 82:2056 (1988).
Bischoff et al., Biochem. Biophys. Res. Commun., 179:628–33 (1991).
Hirai et al., J. Immunol., 141:3958 (1988).
Hirai et al., J. Exp. Med., 172:1525 (1990).
Knauer et al., N. Engl. J. Med., 304:1404 (1981).
Maione et al., Science, 247:77–79 (1990).
Metzger et al., Chapter 35, "Late Phase Asthma in an Allergic Rabbit Model", pp. 347–362, 1990.
Osterman et al., Biochem. and Biophys. Res. Comm., 107(1):130–135 (1982).
Wasserman et al., J. Allergy Clin. Immunol., 74:275–279 (1984).

Primary Examiner—Chhaya D. Sayala
Attorney, Agent, or Firm—Fish & Richardson

[57] ABSTRACT

A method of inhibiting pro-inflammatory mediator release from basophils or mast cells to treat an inflammatory disease in a mammal, comprising administering to the mammal a therapeutically effective amount of one or more of the following proteins, MIP-1α, MIP-1β, CTAP-III, or IP-10.

18 Claims, 5 Drawing Sheets

5,474,983

METHOD OF INHIBITING PRO-INFLAMMATORY MEDIATOR RELEASE FROM BASOPHILS AND MAST CELLS

STATEMENT AS TO FEDERALLY SPONSORED RESEARCH

This invention was made with Government support under Grant No. 1526N awarded by the National Institutes of Health. The Government may have certain rights in the invention.

BACKGROUND OF THE INVENTION

This invention relates to the use of specific proteins to inhibit pro-inflammatory mediator release from basophils and mast cells in mammals.

Basophils and mast cells are "primary allergic" cells in that they release numerous pro-inflammatory mediators that give rise to inflammatory, e.g., allergic, diseases, which include a wide range of disorders such as allergic rhinitis, urticaria, allergic conjunctivitis, atopic dermatitis, and allergic contact dermatitis. One of the most prevalent allergic diseases is asthma. It is estimated that 5% of the population of industrialized countries suffer from asthma. In the United States, reported cases of asthma have risen from 3% in 1979 to 4% in 1987, with over 10 million people currently affected.

Asthma is defined as an inflammation of the airways associated with bronchial hyper-responsiveness and bronchoconstriction, causing intermittent wheezing and coughing. Asthma is associated with airway inflammation, increased mucous secretion, mucosal edema, smooth muscle contraction, mast cell degranulation, and bronchial hyper-responsiveness. It is currently believed that asthma and other allergic diseases are caused by hypersensitivity reactions induced by primary allergic cells, i.e., basophils and mast cells, which are highly specialized effector cells of the immune system. Both cells store and synthesize large quantities of various mediators of inflammation, and express high affinity IgE receptors. These pro-inflammatory mediators include, e.g., histamine, tryptase (from mast cells), leukotrienes ($C_4$, $D_4$, $E_4$), Platelet Activating Factor (PAF), a variety of cytokines, and other neutral proteases.

Basophils and their mediators are involved, for example, in "cutaneous basophil hypersensitivity," and in the so-called "late phase allergic reaction" in the upper airways and skin; however, the mechanism responsible for protracted histamine release seen during this late phase allergic reaction remains obscure. The late phase appears four to six hours after an allergen-dependent immediate hypersensitivity reaction, and it seems that factors other than allergen or IgE antibody are responsible for basophil and/or mast cell secretion during that time.

In 1979, Thueson et al. reported that the crude supernatant of mononuclear cell cultures contain a factor (Histamine Releasing Factor or HRF) which stimulates basophils and/or mast cells to release histamine. *J. Immunol.*, 122:623 (1979). Dvorak et al. later described that HRF is also chemotactic for basophils. *Clin. Immunol. Immunopathol.*, 32:142 (1984). A major constituent of HRF activity is so-called Monocyte Chemotactic and Activating Factor/Monocyte Chemoattractant Protein-1 (MCAF/MCP-1), which is the most potent protein to release histamine from basophils. See, e.g., Kuna et al., *J. Exp. Med.*, 175:489 (1992) and Alam et al., *J. Clin. Invest.*, 89:723 (1992).

HRFs such as MCAF/MCP-1 are thought to contribute significantly to the protracted histamine release and basophil and/or mast cell degranulation seen in a wide variety of immunologic disorders including inflammatory diseases such as scleroderma and rheumatoid arthritis, and allergic diseases such as chronic urticaria, atopic dermatitis, and asthma, although the specific contribution of MCAF/MCP-1 to histamine release in such disorders has not yet been determined. However, MCAF/MCP-1 has been recently reported to be elevated in the synovial fluid of patients with rheumatoid arthritis. Koch et al., *J. Clin. Invest.*, 90:772 (1992). The mean concentration found was 25.5±8.1 ng/ml which corresponds to $3\times10^{-9}$M, at which concentration it is both a chemotactic factor and activates basophils to release histamine.

In addition, other proteins such as RANTES (which stands for "regulated upon" activation, normal T cell expressed and presumably secreted), Connective Tissue Activating Peptide III (CTAP-III), and Interleukin-8 (IL-8) have been shown to induce basophils to release histamine. See, e.g., Kuna et al., *J. Immunol.*, 149:636 (1992); and Bischoff et al., *Biochem. Biophys. Res. Commun.*, 179:628–33 (1991).

Soon after the concept of HRF was reported, mononuclear cell supernatants were also found to contain an inhibitor of HRF-dependent histamine release; the activity was designated Histamine Release Inhibitory Factor (HRIF). Alam et al., *J. Clin. Invest.*, 82:2056 (1988). IL-8 has been shown to fulfill the function attributed to HRIF since preincubation of basophils with IL-8 inhibit HRF and MCAF/MCP-1-induced histamine release. Kuna et al., *J. Immunol.* 147:1920–1924 (1991). More recently, RANTES was shown by applicants, and then others, to inhibit HRF or MCAF/MCP-1 induced histamine release. Kuna et al., *J. Immunol.*, 149:636 (1992); Alam et al., *Am. J. Respir. Cell Mol. Biol.*, 7:427 (1992).

It has also been shown that basophils are "primed" and augment their secretion of histamine if preincubated with Interleukin-3 (IL-3), IL-5, or Granulocyte Macrophage-Colony Stimulating Factor (GM-CSF). See, e.g., Hirai et al., *J. Immunol.*, 141:3958 (1988); Hirai et al., *J. Exp. Med.*, 172:1525 (1990); Dahinden et al., *J. Exp. Med.*, 170:1787 (1989); and Kuna et al., *J. Exp. Med.*, 175:489 (1992).

The treatment of respiratory allergic diseases such as asthma has undergone fundamental changes over the last decade. Emphasis has shifted from making the patient as comfortable as possible by eliminating bronchoconstricting symptoms to treating the underlying condition of the inflammatory response of the airways so as to prevent long-term bronchial destruction. The two primary goals in the management of asthma are to limit bronchial hyper-responsiveness and reduce inflammation of the airways.

First line anti-inflammatory therapy for asthma is the use of inhaled steroids, which are often used concomitantly with inhaled β-agonist-type bronchodilators. Beta-agonists used in this fashion provide prompt relief with few side effects. However, a growing number of studies suggests that one of these β-agonists, fenoterol, may be responsible for an increasing number of deaths of asthmatic patients. Beta-agonists are also contraindicated in patients with coronary disease, as these drugs increase the heart rate. Inhaled cromolyn sodium can be added to such regimens when further therapy is needed. Antihistamines are commonly used to treat allergic rhinitis and urticaria, but often lack complete efficacy and are ineffective against asthma.

Adjunctive therapy includes the use of oral or intravenous theophylline, a bronchodilator used to prevent broncho-constriction, and/or oral β-agonists. These have narrow therapeutic spectrums and side effects are common. Oral corticosteroids are used in refractory patients; however, low doses are not always effective, and high doses have serious adverse effects due to their toxicity. For example, high blood levels of corticosteroids are associated with Cushing's Syndrome, osteoporosis, and cataracts. As a result, none of the currently available treatment regimens are effective in curing asthma, or in substantially avoiding adverse side effects.

SUMMARY OF THE INVENTION

Applicants have discovered that the following proteins RANTES, CTAP-III, the γ-interferon-inducible protein IP-10, and MIP-1α and MIP-1β (human macrophage inflammatory proteins 1α and 1β), inhibit pro-inflammatory mediator release from primary allergic cells, e.g., basophils and mast cells, in a time and dose dependent fashion. These mediators include preformed mediators such as histamine, cytokines, and tryptase (in mast cells), and synthesized mediators such as leukotrienes, prostaglandins, and PAF.

Based on this discovery, applicants have developed a method of inhibiting pro-inflammatory mediator release from basophils or mast cells to treat an inflammatory disease, e.g., an allergic disease, in a mammal, e.g., a human, by administering to the mammal a therapeutically effective amount of one or more of the following proteins, RANTES, MIP-1α, MIP-1β, CTAP-III, or IP-10, or an analog of these proteins, or a peptide fragment of any one of these proteins or analogs. This method substantially avoids adverse side effects and any immunological reaction to the therapy.

As used herein, the term "inflammatory disease" refers to any disease characterized by an increased secretion of pro-inflammatory mediators, compared to a basal level, by primary allergic cells, i.e., basophils and mast cells. The term "inflammatory diseases" includes rheumatoid arthritis, scleroderma, and the allergic diseases, which are inflammatory diseases caused by a specific allergen.

Allergic diseases include respiratory allergic diseases such as asthma and allergic rhinitis ("hay fever"), and various types of urticaria, e.g., cold-induced urticaria, angioedema, allergic conjunctivitis, atopic dermatitis, allergic contact dermatitis, drug allergies, e.g., to penicillin or sulfa drugs, insect sting allergies, and systemic anaphylaxis.

A "therapeutically effective amount" of a protein is a dosage that improves the symptoms of the inflammatory, e.g., allergic, disease by inhibiting the secretion of pro-inflammatory mediators, e.g., histamine, from the primary allergic cells.

In this method, the protein, analog, or peptide fragment may be mixed with a pharmaceutically acceptable carrier, and the protein, analog, or fragment can be administered systemically at a dosage of between 1 to 10 mg/m$^2$ of body surface area, or 0.5 to 500 µg/kg, preferably 20 to 200 µg/kg, of the body weight, of the mammal. The protein, analog, or fragment also can be administered by inhalation at a dosage of between 10 ng to 1 mg, and preferably 100 ng to 100 µg, per inhalation. For topical administration, the dosage is 100 ng to 10 mg/surface area/day.

The protein, analog, or fragment can be administered by intravenous, intraarterial, intramuscular, subcutaneous, oral, or other systemic administration, or by transdermal, intranasal, or other topical administration. The protein, analog, or fragment can also be administered to the mammal together with a different histamine-release inhibiting agent, such as another protein, analog, or peptide fragment, e.g., in the form of a chimeric protein.

The invention also features a method of inhibiting pro-inflammatory mediator, e.g., histamine, release from basophils or mast cells to treat an inflammatory disease in a mammal, e.g., a human, by administering to the human a therapeutically effective amount of a synthetic or recombinant protein having the biological activity, e.g., the ability to inhibit pro-inflammatory mediator release from basophils or mast cells, of any one of the following proteins, RANTES, MIP-1α, MIP-1β, CTAP-III, or IP-10, wherein the protein has the same amino acid sequence of these proteins with the exception of conservative amino acid substitutions.

In addition, the invention features a method of inhibiting allergic disease, e.g., a respiratory allergic disease, in a mammal, e.g., a human, by administering a therapeutically effective amount of one or more of the following proteins, RANTES, MIP-1α, MIP-62, CTAP-III, or IP-10, or an analog of these proteins, or a peptide fragment of any one of these proteins or analogs.

The respiratory allergic disease treated according to this method may be asthma, and the protein, analog, or fragment can be administered by inhalation at a dosage of between 10 ng to 1 mg, and preferably 100 ng to 100 µg, per inhalation.

Other features and advantages of the invention will be apparent from the detailed description, and from the claims.

DETAILED DESCRIPTION

Figure 1:
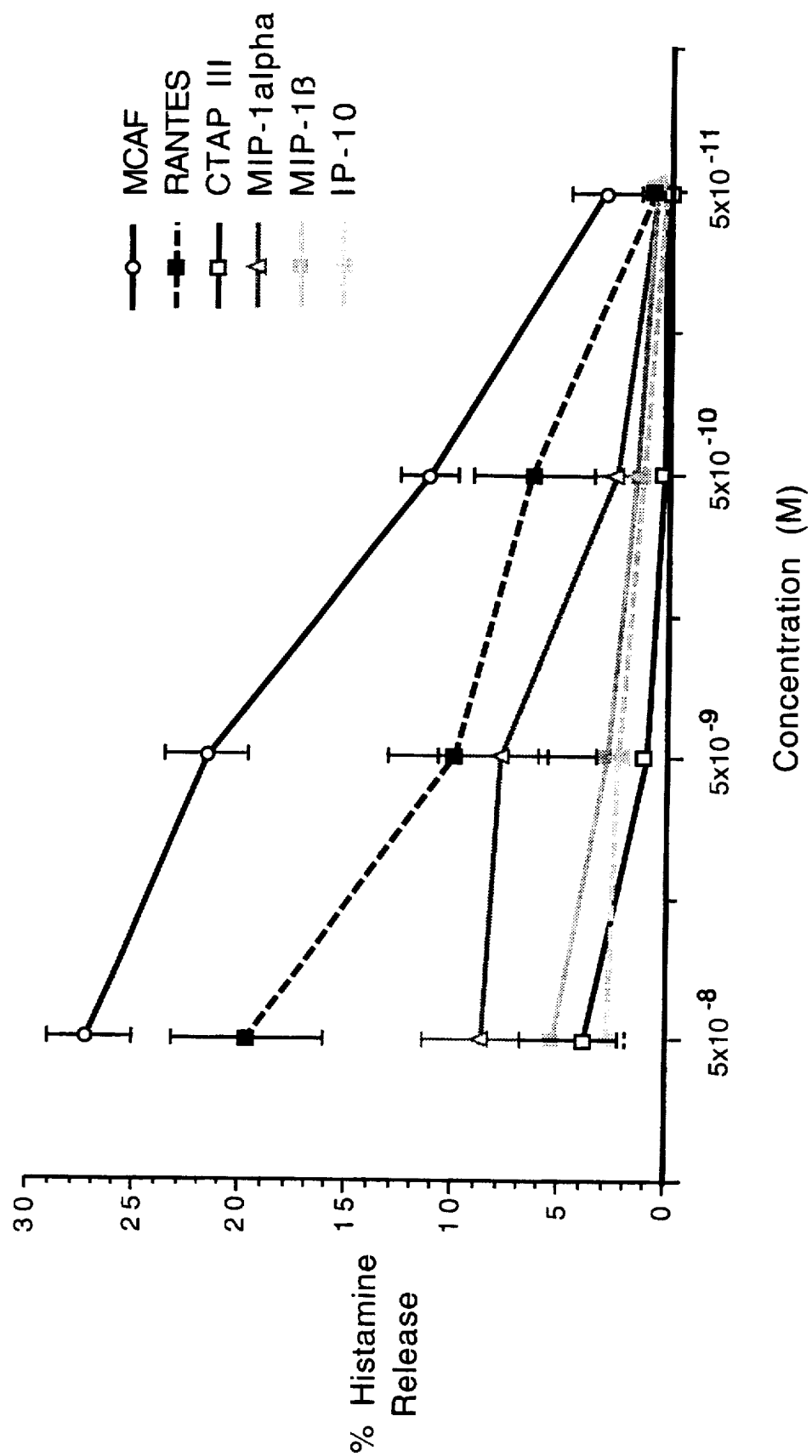
FIG. 1 is a graph showing dose dependent histamine release by MCAF/MCP-1,RANTES, CTAP-III, MIP-1α, MIP-1β, and IP-10.

Applicants have discovered that the following proteins RANTES, CTAP-III, IP-10,MIP-1α, and MIP-1β, inhibit or decrease the release of pro-inflammatory mediators, e.g., histamine, from primary allergic cells, e.g., basophils and mast cells, in a time and dose dependent fashion. More importantly, based on these results, applicants have discovered that this inhibition can be used to treat inflammatory diseases such as allergic diseases like asthma in humans and other animals.

Preparation of Proteins

All of the proteins of the invention can be prepared by standard recombinant techniques. The amino acid sequences of RANTES, MCAF/MCP-1,CTAP-III, IP-10,MIP-1α, and MIP-1β are published. See, e.g., Oppenheim, et al., *Annu. Rev. J. Immunol.*, 9:617–648 (1991), which is incorporated herein by reference. In addition, recombinant human MCAF/MCP-1 (rh-MCAF/MCP-1), with a maximal chemotactic activity on human monocytes at 20 ng/ml, can be purchased from Pepro Tech Inc., Rocky Hill, N.J.

For example, recombinant human RANTES, MIP-1α, and MIP-1β were produced in *E. coli* by linking a cDNA encoding the mature, secreted form of the molecule (devoid of the mammalian signal sequence) to the bacterial ST II promoter in an expression plasmid. After transformation and growth, RANTES was isolated from cell pastes which were harvested in 0.25M sodium acetate buffer, pH 3.0,and the cells disrupted at high pressure in a fluidizer. After centrifugation, the supernatant from this lysate was filter clarified and applied to an S-Sepharose fast flow column at pH 6.0. Eluates obtained by salt gradient were subsequently subjected to reverse phase HPLC, and eluted fractions assayed using a RANTES antipeptide antibody. Positive fractions were pooled, precipitated with ammonium sulfate, subjected to a 5 kD tangential diaflow filtration, and resuspended in 450 mM NaCl, 10 mM Na Citrate formulation buffer at pH 5.0. Preparations of purified RANTES contained less than 1 endotoxin unit/mg of protein as determined by the Limulus amebocytes lysate reaction.

Human MIP-1α and MIP-1β were isolated from the supernatants of *E. coli* culture using methods described for the natural MIP-1 protein in Wolpe et al., *J. Exp. Med.,* 167:570 (1988), which is incorporated herein by reference.
Production of Protein Analogs That Inhibit Mediator Release It is known that proteins of identified structure and function may be constructed by changing the amino acid sequence if such changes do not significantly alter the protein secondary structure. Kaiser et al., *Science*, 223:249–255 (1984). Accordingly, the subject invention includes analogs (mutants) of the naturally occurring proteins RANTES, CTAP-III, IP-10,MIP-1α, and MIP-1β, and peptide fragments thereof, which exhibit substantially the same, lower, or higher histamine release inhibiting activity of the naturally occurring or recombinant proteins.

Synthetic genes encoding mutant analogs that have the ability to inhibit pro-inflammatory mediator release from primary allergic cells, e.g., basophils, can be constructed by changing the codons for specific residues in the sequence of the naturally occurring protein, to sequences encoding different amino acids, e.g., by cassette mutagenesis. Such analogs include a portion of the natural sequence and must have the ability to inhibit the release of histamine by basophils. Such analogs can be tested for efficacy for the methods of the invention in the in vitro histamine assay described below, or in the in vivo rabbit asthma model, also described below.

Analogs according to the invention may include conservative amino acid substitutions, as long as the analog has a histamine release inhibiting activity. For example, the analog may include a terminal methionine not found in the naturally occurring protein. As used herein, the term conservative amino acid substitution means the substitution of an amino acid with another amino acid that is of the same class. Amino acids may be placed in the following classes: basic, hydrophobic, acidic, polar, and amide. Substitutions in which an amino acid of one class is replaced with another amino acid of the same class fall within the scope of the subject invention, so long as the substitution does not materially alter the biological activity of the compound. Table I below provides a listing of examples of amino acids belonging to each class.

TABLE I

| Class of Amino Acid | Example of Amino Acids |
| --- | --- |
| Basic | Lus, Avg, His |
| Hydrophobic | Ala, Leu, Ile, Val, Pro, Phe, Trp, Tyr, Met |
| Acidic | Alu, Asp |
| Polar | Ser, Thr, Asa, Gln, Cys |
| Amide | Gln, Asn |

To use a synthetic gene encoding a mutant analog, linkers may be included on each end of the synthetic gene to facilitate the directional insertion into a vector. The mutant protein can be expressed, cleaved, and extracted by standard techniques. For example, cells expressing the analog protein may be subjected to lysozyme (1 mg/g cells), DNase I (500 units/100 g cells) and bead mill treatments. The resulting lysis pellet containing the protein is treated with CNBr (10 g/100g cells) in 70% formic acid to cleave the protein from any undesired portions. Following evaporation of the CNBr/formic acid, the recombinant protein is extracted with 200 ml of 50 mM Tris-Cl,pH 7.6, 5 mM EDTA, and 10 mM DTT per 100 g of cell starting material. The extracts are then purified using ion-exchange chromatography, and eluted with a gradient of 0–1M NaCl. Such analog proteins are then dialyzed into 20 mM acetate buffer, pH 5.0. The samples are further purified by reverse phase HPLC.

The protein analogs of the invention can also be synthesized by standard techniques as described below with respect to peptide fragments.
Peptide Fragments of the Proteins of the Invention Peptide fragments of the proteins, or analogs, of the invention, also can be used in the methods of the present invention. A peptide fragment is some portion of the full length native or recombinant protein, or mutant analog, that has substantially the same, lower, or preferably higher, ability as the native protein to inhibit histamine release from basophils. These peptides can be prepared by standard solid phase synthesis procedures, e.g., using an Applied Biosystems Inc. 430 automated synthesizer according to standard methods using Boc/benzyl protected amino acids and anhydrous hydrogen fluoride cleavage/deprotection. See, e.g., Stewart et al., *Solid Phase Peptide Synthesis*, Pierce Chemical Com. Rockford, Ill., 1984.

The peptide fragments are then cleaved from the solid support and deblocked, and purified to greater than 98% homogeneity by one pass over a 2×25 cm reverse phase HPLC column (Vydac) using a water/acetonitrile (0.1% trifluoroacetic acid) gradient. Peptides can be identified and quantitated using a Waters Picotag (Milford, Mass.) amino acid analysis system and Electrospray Mass spectrometry, according to standard methods.

Synthetic peptide fragments corresponding to sequences of proteins as small as 13 amino acids in length may be useful for the methods of the invention, as long as they have the ability to inhibit histamine release from basophils. The use of short peptides offer several advantages over whole proteins, such as reduced dosage (weight basis), reduced likelihood of antigenicity, and greater likelihood of effectiveness in novel dosage forms. Additionally, since small peptide fragments are generally less antigenic than larger proteins, short peptides can be used advantageously for oral and transdermal administration.

Using the methods of this application, a researcher could prepare and readily test analogs and peptides which could be expected to have the desired properties. In addition, amino acid substitutions in the full length protein analogs can also be incorporated in such peptide fragments.

Purification of CTAP-III

CTAP-III was purified according to the procedure described by Reddigari et al., *J. Allergy Clin. Immunol.*, 89:666 (1992), which is incorporated herein by reference. Platelets were isolated from normal human donors, suspended in PBS containing 1 mM EDTA, 5 mM glucose and 0.1 mM PMSF (Sigma, St. Louis, Mo.), and stimulated with 20 µM calcium ionophore A-23187 (Sigma), at 37° C. for 30 min. according to Coller et al., *J. Clin. Invest.*, 72:325 (1983). MAb #18-1 to CTAP-III (Baeza et al., *J. Clin. Invest.*, 85:1516 (1990)), was coupled to tresyl activated agarose (10 mg IgG/ml of Affinica™ gel, Schleicher and Schuell, Inc., Keene, N.H.) in 0.2M NaHCO$_3$, 0.5M NaCl pH 8.5 according to the manufacturer's recommendations. The gel was equilibrated with 0.01M sodium phosphate buffer, pH 7.5 containing 0.5M NaCl mM PMSF, 0.1 mM EDTA and 0.02% azide (equilibration buffer). Platelet releasate was applied to the column and washed with the equilibration buffer until the A$_{280}$ nm of the wash fractions returned to the baseline. 0.5 ml fractions were then eluted with 3.0M potassium thiocyanate and peak protein fractions were pooled, dialyzed against PBS (pH 7.4) containing 0.1 mM PMSF, and stored at −70° C. Purity of CTAP-III was greater then 95% as determined by SDS-PAGE.

Cell Preparation

The procedure for leukocyte isolation has been described previously, Kaplan et al., *J. Immunol.*, 135:2027 (1985), which is incorporated herein by reference. Briefly, the cells were prepared by dextran sedimentation (0.6% dextran, 0.6% glucose, 0.02M EDTA), the basophil containing layer was washed twice with HEPES-buffered saline containing 0.3% HSA (HBS-HSA), and the cells were resuspended in HBS-HSA containing 2 mM CaCL$_2$ and 2 mM MgCl$_{12}$. In some experiments basophils were purified from peripheral blood on a discontinuous Percoll gradient according to the method described by Leonard at al., *J. Leuk. Biol.*, 35:169 (1984), followed by negative selection using magnetic beads coated with goat anti-mouse IgG (Advanced Magnetic Inc., Cambridge, MA). The basophils purified by Percoll gradient were incubated in D-PBS, pH 7.4 containing 1% BSA (D-PBS-BSA) plus a mixture of mAb directed against T lymphocytes, B lymphocytes and monocytes (anti-Leu-5b (CD2), anti-Leu-16 (CD20), and anti-Leu-M3 (CD14)(Becton Dickinson, San Jose) for 45 min. at 4° C. The cells were then washed three times in ice-cold D-PBS-BSA, resuspended in 1.0 ml medium, and incubated in a head over head rotor with goat anti-mouse IgG coated magnetic beads (ratio beads:cells 50:1) for 30 min. at 4° C. The immunomagnetic rosetted cells were removed from suspension by a magnetic field. Rosetted cells were collected and resuspended gently into the incubation medium. The magnetic separation was repeated to remove the immunomagnetic rosetted cells from remaining basophils to increase their recovery. The two basophil-containing supernatants were combined, the cells washed twice, and the entire procedure was repeated once again. The purity of the final basophil suspension was determined by staining with alcian blue and was 80%.

Assay of Histamine Release from Basophils

One hundred microliters of cells, resuspended in HBS-HSA with 2 mM CaCl$_2$ and 2 mM MgCl$_2$ and prewarmed to 37° C. were added to 20 µl of tested protein at the given concentration. For inhibitory or priming experiments, the cells were preincubated with each factor or buffer for 10 min. (except for kinetic experiments) at 37° C. followed by addition of 20 µl MCAF/MCP-1,anti-IgE (affinity purified goat anti human IgE antibody (Kirkegaard & Perry Laboratories Inc., Gaithersburg, Md.), or buffer. After incubation the supernatants were separated by centrifugation at 700×g for 5 min at 4° C. and histamine release determined. Two replicate aliquots of cells were boiled to determine total basophil histamine content. All histamine release experiments were performed in duplicate and the results expressed as a percentage of total histamine content. Spontaneous histamine release from the cells was less than 5% and was subtracted from the calculated histamine release.

A radioenzyme assay for histamine was performed in duplicate for each sample by using a modification of the method of Beaven et al., *Clin. Chem. Acta.*, 37:91 (1972), as described previously in Kuna et al., *J. Immunol.*, 149:636 (1992), which are both incorporated herein by reference. Although only histamine was assayed, this released histamine also indicates that other preformed (granule), and subsequently synthesized, pro-inflammatory mediators are being released by the basophils. The latter may require priming the basophils by Interleukin-3,which is likely to occur in vivo in allergic patients.

Statistical analysis

Results were expressed as mean ± SEM. Statistical analysis was performed with Wilcoxon's Signed Rank Test or Student's t-Test paired (as indicated in the text) using the computer program StatWorks (Cricket Software, Philadelphia, Pa.).

Protein-Dependent Histamine Release

The ability of various proteins to stimulate histamine release was assessed as indicated in FIG. 1. Human basophils were incubated with each protein at concentrations ranging from $5\times10^{-8}$ to $5\times10^{-11}$M and the percentage of histamine release determined. Each point represents the mean ±SEM of six experiments performed in different donors. MCAF/MCP-1 and RANTES are clearly positive. Thus, MCAF/MCP-1 released more than 10% histamine starting at $5\times10^{-10}$M while RANTES released more than 10% histamine at $5\times10^{-9}$M and above. Histamine release induced by MIP-1α was borderline, and at a concentration of $5\times10^{-8}$M and $5\times10^{-9}$M released 8.8±3.1% histamine. MIP-1β, CTAP-III, and IP-10 were clearly negative at the concentrations studied.

Dose-dependent Histamine Release Inhibition by Proteins

The effect of preincubation of basophils with various proteins ($5\times10^{-8}$ to $5\times10^{-1}$M) upon MCAF/MCP-1 induced histamine release was assessed and the results shown in Table II, below. All tested proteins inhibited MCAF/MCP-1-induced histamine release in a dose dependent fashion.

TABLE II

PERCENTAGE OF HISTAMINE RELEASE INHIBITION
Concentration of Proteins to which MCAF at $10^{-7}$ was added
(MCAF at $10^{-7}$M released 30.1 ± 2.2% histamine)

|  | $5 \times 10^{-8}$M | $5 \times 10^{-9}$M | $5 \times 10^{-10}$M | $5 \times 10^{-11}$M |
|---|---|---|---|---|
| MCAF | 100* | 100* | 100* | 61.5 ± 2.7* |
| RANTES | 59.5 ± 4.5** | 69.2 ± 3.5* | 51.2 ± 3.9* | 24.6 ± 2.7* |
| MIP-1α | 48.2 ± 4.1** | 48.8 ± 3.1* | 42.2 ± 2.6* | 21.0 ± 3.1*** |
| MIP-1β | 45.9 ± 1.4** | 42.8 ± 3.1* | 26.3 ± 2.3* | 13.6 ± 2.7 |
| CTAP III | 49.6 ± 2.3* | 27.0 ± 4.4 | 25.6 ± 3.8 | 14.3 ± 3.5 |
| IP-10 | 30.9 ± 2.6* | 15.3 ± 2.6** | 11.0 ± 2.1** | 5.4 ± 2.2 |

[(*)-p < 0.014; ()-p < 0.023; (*)-p < 0.037 Wilcoxon's rank sum test]

The most potent inhibitor protein was a low concentration of MCAF/MCP-1, which completely desensitized (which was set as 100%) basophils to high concentrations of MCAF/MCP-1 at an optimal dose range of $5 \times 10^{-8}$ to $5 \times 10^{-10}$, which is 2 to 200 fold lower than the optimal MCAF/MCP-1 dose required for histamine release. However, at these concentrations, MCAF/MCP-1 itself releases significant (more than 10%) percentage of histamine (FIG. 1). At 5×10hu −11M, MCAF/MCP-1 decreased histamine release by 61.5±2.7%, yet induced less than 5% release.

RANTES and MIP-1α were next in potency as inhibitors of MCAF/MCP-1-induced histamine release. At a concentration of $5 \times 10^{-9}$M they inhibited histamine release by 69.2±3.5% and 48.8±3.1%, respectively. At this concentration RANTES released 10±3.8% histamine, and MIP-1α released 8.2±3.1% histamine. MIP-1β, CTAP-III, and IP-10 were more effective at the highest concentration studied ($5 \times 10^{-8}$M), and none of them released a significant amount of histamine.

Kinetics of Histamine Release Inhibition by Proteins

Figure 2:
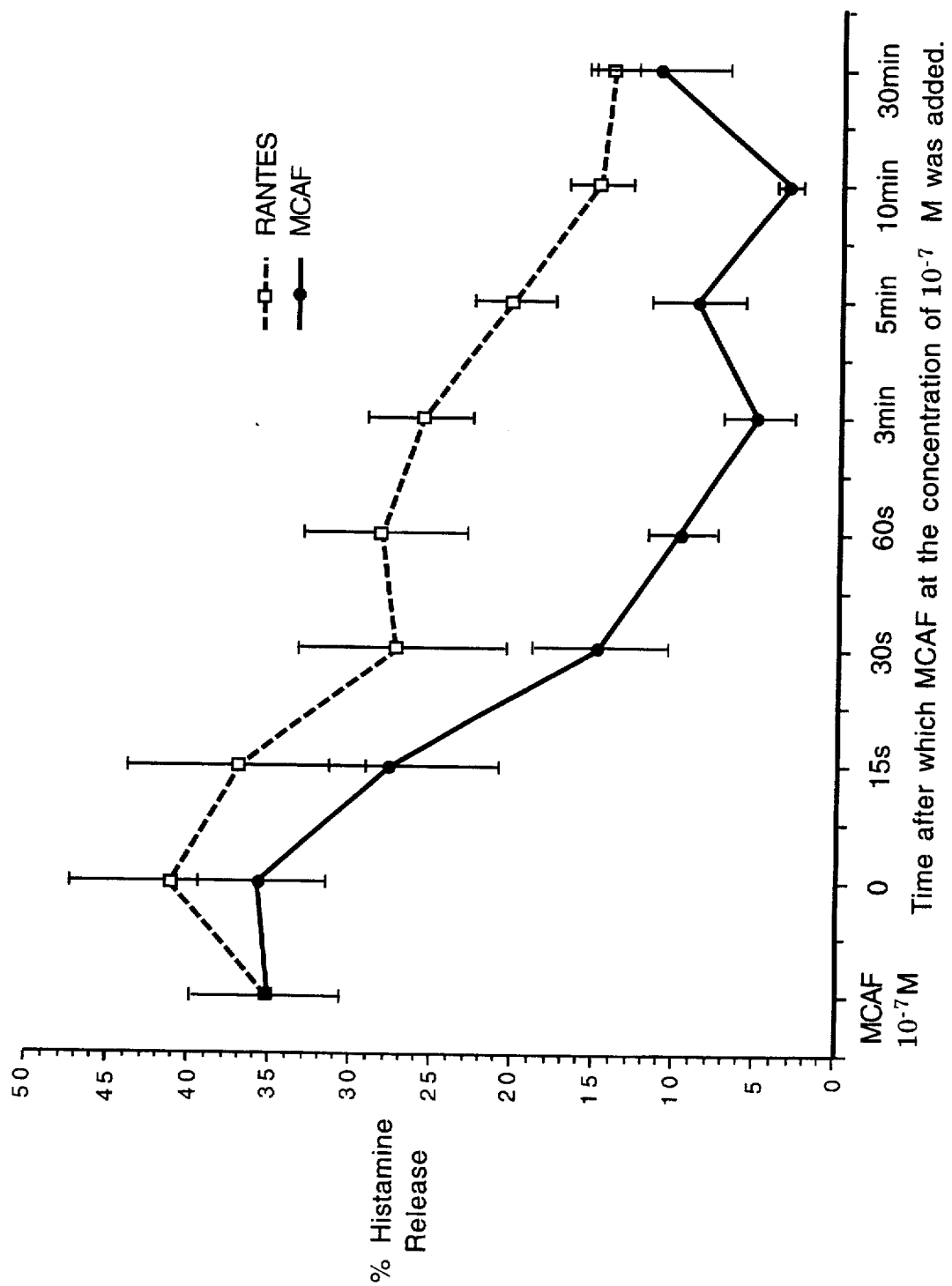
FIG. 2 is a graph showing the kinetics of inhibition of MCAF/MCP-1-induced histamine release by low concentration of MCAF and RANTES.

A time course of inhibition of MCAF/MCP-1-induced histamine release by low concentrations of MCAF/MCP-1 and RANTES is shown in FIG. 2. Leukocytes were preincubated with MCAF/MCP-1 ($5 \times 10^{-10}$M) or RANTES ($5 \times 10^{-9}$M) for 0 sec., 15 sec., 30 sec., 1 min., 3 min., 5 min., 10 min., 30 min., and then MCAF/MCP-1 ($5 \times 10^{-7}$M) was added for 40 minutes. Each point on the graph represents the mean±SEM of six experiments performed in different donors. The inhibition of histamine release by low concentration of MCAF/MCP-1 was very fast and reached a statistically significant difference in 15 seconds. The peak of inhibition was reached after 3 minutes of preincubation and was sustained thereafter. RANTES inhibited histamine release in slower fashion. Inhibition was statistically significant after 3 minutes of preincubation and reached a maximum 10 to 30 minutes after the cells were added.

The results of kinetics studies of inhibition by all the proteins are shown in Table III, below.

TABLE III

| | HISTAKINE RELEASE INDUCED BY MCAP AT $10^{-7}$M | | | |
|---|---|---|---|---|
| Time | 0 | 3 min | 5 min | 10 min |
| MCAF $5 \times 10^{-10}$M | 35.7 ± 4.2 | 4.6 ± 2.4‡ | 7.8 ± 3.1‡ | 2.7 ± 0.9‡ |
| RANTES $5 \times 10^{-9}$M | 41.3 ± 6 | 25.9 ± 3.5§ | 20.2 ± 3.4‡ | 15.3 ± 2.6‡ |
| MIP-1α $5 \times 10^{-9}$M | 44 ± 7.9¶ | 24.9 ± 6.2 | 20.2 ± 3.6§ | 17.2 ± 3.1‡ |
| MIP-1β $5 \times 10^{-9}$M | 40.4 ± 4.5‡ | 30.4 ± 3.7 | 21 ± 2.9‡ | 18.7 ± 2.1‡ |
| CTAP III $5 \times 10^{9}$M | 43.4 ± 5.8‡ | 33.2 ± 3.4 | 25.8 ± 2.7§ | 21.2 ± 2.1‡ |
| IP-10 $5 \times 10^{-9}$M | 45.8 ± 7§ | 32.2 ± 3.8 | 26.2 ± 3.2‡ | 22 ± 2.7‡ |

[(§)-p < 0.023; (¶)-p < 0.037; Wilcoxon's rank sum test]

When low concentrations of the various proteins were mixed with MCAF/MCP-1 at a concentration of $10^{-7}$M, and added to the leukocytes (time 0), the histamine release by this mixture was significantly higher than histamine release by MCAF/MCP-1 alone (MCAF/MCP-1, 35.7±4.2%; MCAF/MCP-1 +RANTES, 41.3±6%; MCAF/MCP-1+MIP-1α, 44±7.9%; MCAF/MCP-1 +MIP-1β, 40.4±4.5%; MCAF/MCP-1+CTAP-III, 43.4±5.8%; MCAF/MCP-1+ IP10, 45.8±7%). Once the proteins were preincubated with the cells prior to challenge with MCAF/MCP-1, a statistically significant inhibition of histamine release was reached at about 5 minutes of preincubation with all proteins except with RANTES, which required only 3 minutes of preincubation. The peak of inhibitory activity was attained after 10 minutes preincubation and remained unchanged (a lack of statistically significant difference) up to 30 minutes of preincubation.

The Effect of Proteins on MCAF/MCP-1 and Anti-IgE Induced Histamine Release

Figure 3:
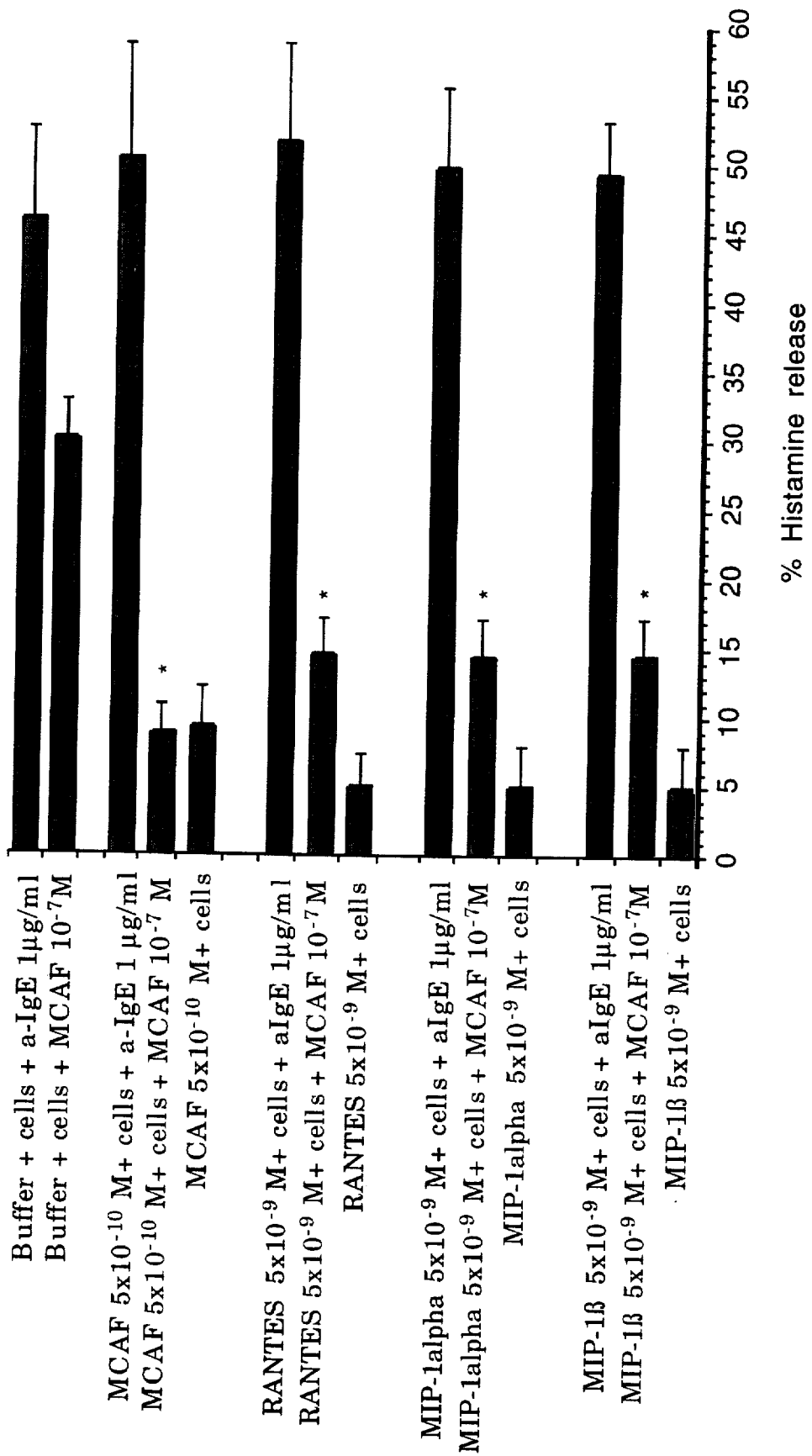
FIG. 3 is a graph showing the effect of proteins MCAF/MCP-1,RANTES, MIP-1α, and MIP-1β on histamine release induced by anti-IgE and MCAF/MCP-1.

Leukocytes from 13 subjects were tested for inhibition or enhancement of histamine release due to the proteins of the invention. The results are presented in FIGS. 3 and 4. As shown in FIG. 3, proteins MCAF/MCP-1, RANTES, MIP-1α, and MIP-1β, inhibit MCAF/MCP-1, but not anti-IgE induced histamine release under the particular in vitro test conditions. Leukocytes were preincubated with either buffer alone, MCAF/MCP-1 ($5 \times 10^{-10}$M), RANTES ($5 \times 10^{-9}$ M), MIP-1α ($5 \times 10^{-9}$M), or MIP-1β ($5 \times 10^{-9}$M) for 10 minutes at 37° C. Next, the cells were challenged with anti-IgE (1 µg/ml) or MCAF/MCP-1 ($10^{-7}$M). The results obtained from 13 subjects are expressed as the mean percentage of histamine release ±SEM. Statistical significance is shown versus histamine release induced by MCAF $10^{-7}$M; (*) p<0.001 (Student's t-test paired).

Figure 4:
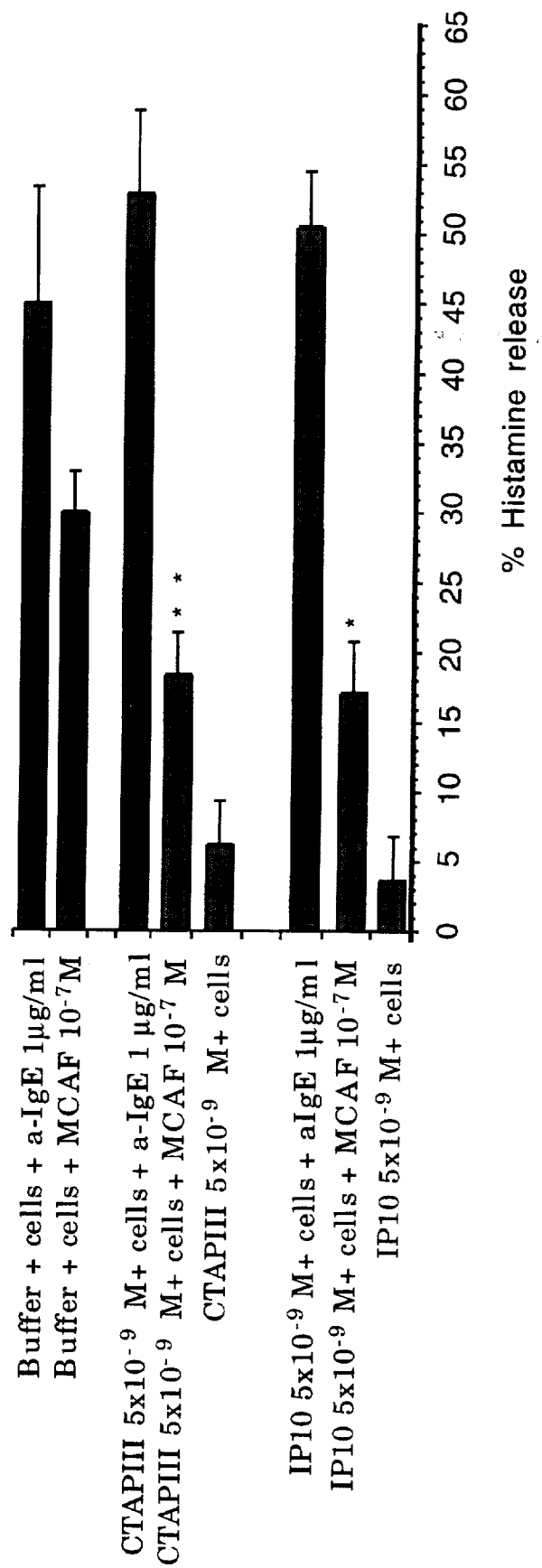
FIG. 4 is a graph showing the effect of proteins CTAP-III and IP-10 on histamine release induced by anti-IgE and MCAF/MCP-1.

FIG. 4 shows the effect of the proteins CTAP-III and IP-1o on anti-IgE and MCAF/MCP-1 induced histamine release. Here too the proteins inhibited histamine release induced by MCAF/MCP-1,but not by anti-IgE, under these particular in vitro conditions. Leukocytes were preincubated with either buffer alone, CTAP-III ($5 \times 10^{-9}$M), or IP-10 ($5 \times 10^{-9}$M) for 10 minutes at 37° C, and then challenged with anti-IgE (1 µg/ml) or MCAF/MCP-1 ($10^{-7}$M). Statistical significance is shown versus histamine release induced by MCAF/MCP-1 $10^{-7}$M; (*) p<0.001; (**) p≦0.007. These results confirmed and enlarged upon the data obtained from our dose response and kinetics study.

Inhibition of Histamine Release by Proteins Using Purified Basophils

Figure 5:
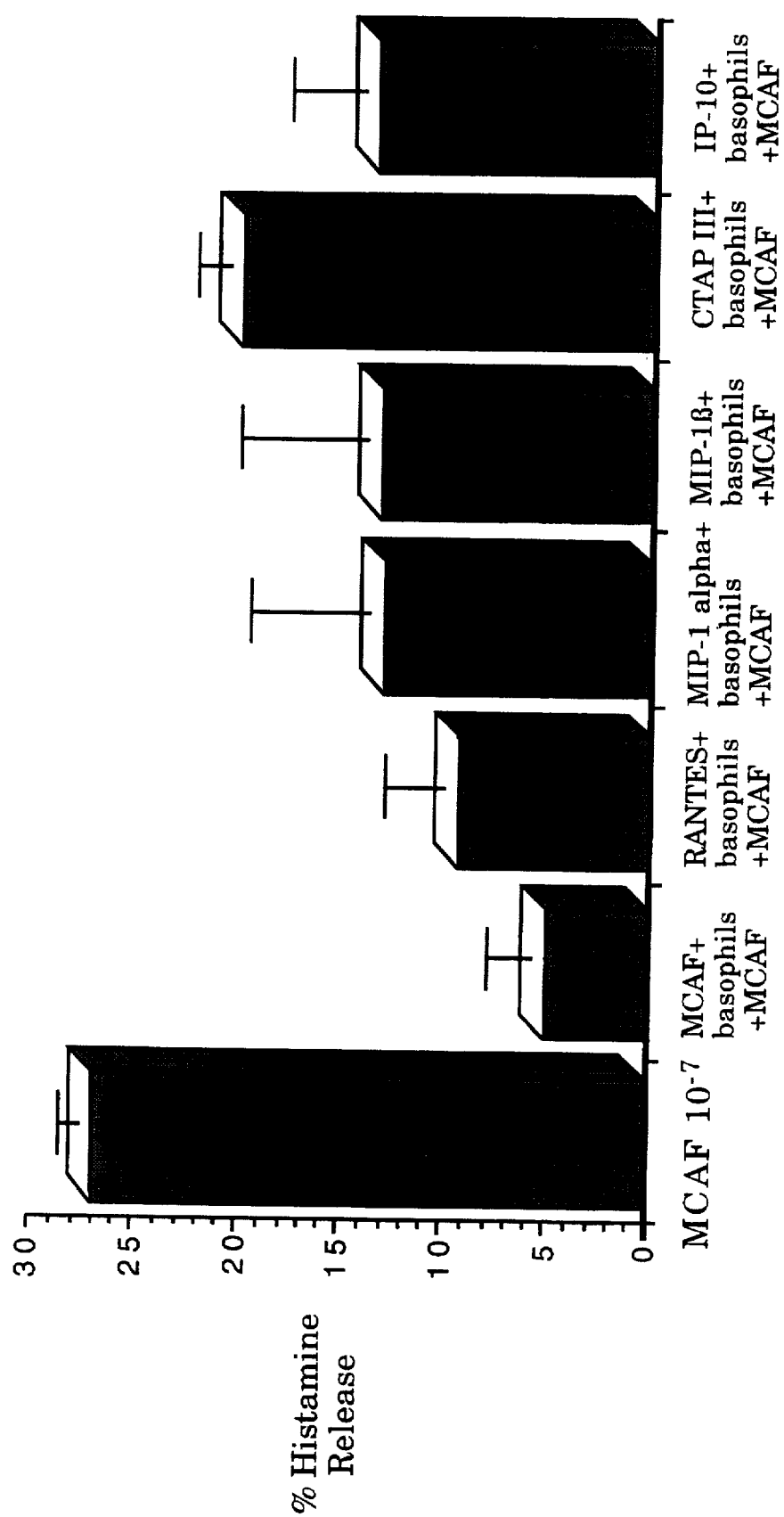
FIG. 5 is a graph showing protein-dependent inhibition of MCAF/MCP-1-induced histamine release from basophils purified to 80%.

The proteins of the invention have various target cells. To determine whether the inhibitory effect seen with these proteins is due to a direct interaction with basophils, we preincubated basophils at 80% purity with the proteins for 10 minutes, after which MCAF/MCP-1 at a concentration of $10^{-7}$M was added (FIG. 5). Cells were preincubated with either MCAF/MCP-1 ($5 \times 10^{-10}$M), RANTES ($5 \times 10^{-9}$M), MIP-1α ($5 \times 10^{-9}$M), MIP-1β ($5 \times 10^{-9}$M), CTAP-III ($5 \times 10^{-9}$M), or IP-10 ($5 \times 10^{-9}$M) for 10 minutes at 37° C. and then challenged with MCAF/MCP-1 ($10^{-7}$M) for 40 minutes. Bars represents mean±SEM from four experiments in different donors. A similar pattern of inhibition was seen as with mixed leukocytes in which the percentage of basophils was 0.5–2.0%.

Animal Tests

A widely used animal model of human asthma is the rabbit model described in W. Dorsch, *CRC Handbook on Late Phase Response*, Chap. 35 (1990), which is incorporated herein by reference. In addition, Irvin, *J. Allergy Clin. Immunol.*, 90(3):521–533 (1992), describes a rabbit model for sinusitis, which is incorporated herein by reference.

To test the effectiveness of the proteins, and analogs or peptide fragments thereof, of the invention to control asthma, the rabbit asthma model can be used with an aerosol or other challenge with the specific protein or combination of proteins. In order to induce an early- and late-phase asthmatic response, allergic rabbits are anesthetized and restrained on a molded surgical board in the supine position. They are intubated after the method of Zavala et al., *Proc. Soc. Exper. Biol. Med.*, 144:509 (1973), and an esophageal balloon is placed to record transpulmonary pressures and flow. These are used to calculate dynamic compliance ($C_{dyn}$) and total lung resistance ($R_1$) after the method of Davidson et al., *J. Appl. Physiol*, 21:1094 (1966). A Buxco® analyzer may be used for automated calculations.

For measurements of allergen sensitivity and demonstration of late responses, the allergen is nebulized with the DeVilbiss® nebulizer (10,000 PNUs/ml) for 30 s, then for 2 min. separated by 5 min. observation periods. When the transpulmonary pressure has doubled from baseline, the allergen challenge is stopped. For measurements of nonspecific bronchial hyper-responsiveness (NSBHR), histamine is aerosolized for periods of 2 minutes, interposed by 3 minutes of observation, with 0.075–80 mg/ml concentrations of autocoid. Airway sensitivity is estimated by calculating the dose of histamine or allergen in mg/ml which is required to reduce the $C_{dyn}$ by 50% ($PC_{50}C_{dyn}$ histamine, allergen).

Airway reactivity is calculated from the slope of the dose response curve after the method of Oreheck et al., *Am. Rev. Respir. Dis.*, 115:937 (1977). The severity and duration of a late-phase asthmatic response (LAR) is qualified by calculating the area (mm$^2$) under the curve described by the late response from 1–6 h for $C_{dyn}$ as previously described in Metzger et al., *Chest*, 88:369 (1985), with the use of a Sigmaplot™ digitizer.

Peripheral blood is obtained throughout challenges from a cannulated ear artery with the use of a Heparin lock, and bronchoalveolar lavage is performed at various times from baseline throughout the challenge, and following challenges, via a small polyethylene catheter inserted into the lung until resistance is felt. Suction is applied through a sterile trap and cells obtained from the bronchoalveolar lavage fluid are cytocentrifuged (Cytospin II, Shandon, P. A. Sweickley), and stained with a Geimsa stain (Dif Quick) or Toludine blue (pH 0.5). For tissue samples, staining for mast cells is carried out after preservation with Carnoy's medium and stained with Toludine blue. Normally, tissue preservation is accomplished with 2.5% glutaraldehyde prior to embedding with JB-4 or Spurr's plastic.

To test a particular protein, or analog or peptide fragment thereof, the rabbit from the above model is challenged with an allergen, and then treated with a dosage of 100 ng to 1 mg of the protein/inhalation 8 days later. For other modes of administration, the dosage should be about 10 µg to 10 mg/dose. Two weeks later, the same dosage of protein is again administered, and the rabbit is then challenged with the same allergen 30 minutes later. The $C_{dyn}$, $R_1$, and $PC_{50}$ are measured before the initial administration of the allergen, and at 24 h, 1 week, and 2 weeks after the second administration of the allergen. An improvement in one or more of the $C_{dyn}$, $R_1$, and $PC_{50}$ of greater than about 20% compared to a control indicates that the protein is effective iv vivo. However, any statistically significant clinical improvement can be used as an indication of efficacy.

Therapy

Administration

The invention is carried out by administering a therapeutically effective amount of a protein, or a histamine-release inhibiting analog or peptide fragment thereof, to a patient with an inflammatory disease. Administration may be by various routes, including, e.g., inhalation of an aerosol (intrabronchial or intranasal), intranasal drops, injection, e.g., intravenous, intraarterial, subcutaneous, intramuscular, or intradermal, or topical application to an affected area of skin or eye. As with any treatment for allergic diseases such as asthma, effective dosage schedules should be tailored to meet the patient's needs, and raised or lowered in proportion to his or her propensity to develop acute episodes, the goal being to maintain the best state of pulmonary function with the minimum amount of treatment.

For inhalation, which is the preferred method of administration for respiratory allergic diseases such as asthma (oral inhalation) and allergic rhinitis (intranasal inhalation), the specific protein or analog is solubilized and loaded into, e.g., an atomizer or nebulizer, or a pressurized aerosol dispenser, for administration. Such devices are well known in this field. The protein, analog, or peptide fragment, can also be mixed with a pharmaceutically acceptable carrier, e.g., saline. Dosages for a therapeutically effective amount for inhalation range from 100 ng to 1 mg, and preferably 100 ng to 100 µg, per inhalation. Since the proteins of the invention have no known toxic or immunological side effects, a wide range in dosage is appropriate.

For topical administration, e.g., for atopic dermatitis, contact dermatitis, allergic conjunctivitis, urticaria, or any skin lesion that contains mast cells, a therapeutically effective amount of one or more of the proteins of the invention is applied to the site of skin or eye, or is combined with a pharmaceutically acceptable carrier, e.g., a spreadable cream, gel, lotion, or ointment, or a liquid such as saline. For use on the skin, the penetration of the protein into the diseased tissue may be accomplished by a variety of methods known to those of ordinary skill in this field. For example, the protein may be applied directly and mechanically rubbed into the skin. Furthermore, the protein may be incorporated into a transdermal patch that is applied to the diseased skin. Preferably, the penetration resulting from these methods is enhanced with a chemical transdermal delivery agent such as dimethyl sulfoxide (DMSO) or the nonionic surfactant, n-decylmethyl sulfoxide (NDMS) as described in Choi et al., *Pharmaceutical RES.*, 7(11): 1099–1106 (1990). Dosages for a therapeutically effective amount for topical application would be in the range of 100 ng to 10 mg per treated surface area or lesion per day.

For systemic administration, an effective amount of protein according to the invention is selected to achieve a concentration of 10 ng to 1 mg/ml in the patients blood, and preferably 400 ng to 1 mg/ml. As is known in the medical field, the proper dosage to achieve this blood level of the protein is best determined by the patient's total skin surface area or weight. The total surface area is based on the patient's weight and height and is determined by calculation tables. See, e.g., Harrison, *Internal Medicine*. The average person's surface area is about 1.7 m². Based on this calculation, the dosage should be in the range of 0.1 to 10 mg/m² of body surface area. If based on only a patient's weight, the dosage should be in the range of about 0.5 to 500 µg/kg, preferably 20 to 200 µg/kg. These dosages would be administered on a periodic basis, e.g., daily, weekly, or monthly, depending on clinical symptoms and the patient's response to treatment. Oral dosages would be 5 to 100 times higher than the dosages for injection.

For injection, the proteins are preferably mixed with one or more pharmaceutically acceptable carriers, for example, saline or a physiologic buffer, which are known to those of skill in the art. Of course, in some cases, it may be desirable to incorporate a preservative into this excipient. In addition, the proteins of the invention can be administered systemically or locally by known sustained-release matrices. Methods for incorporating therapeutic agents, such as the proteins of the invention, into pharmaceutical carriers and sustained-release matrices are well within the skill of the art.

Combinations of Proteins

Our results suggest that all of those proteins tested are capable of binding to basophils, but that only MCAF/MCP-1 and RANTES activate the cells at the concentration utilized. Activation has also been reported for CTAP-III/NAP-2 or MIP-1α and β, but higher concentrations are required. MCAF/MCP-1 has 1700±600 binding sites/monocytes with a $K_d$ of 1.9±0.2 nM, and the receptor for MCAF/MCP-1 appears to be distinct. Yoshimura et al., *J. Immunol.*, 145:292 (1990). The great number of cell surface receptors for these proteins on basophils and mast cells indicates that combinations of one or more different proteins should also be useful in the methods of the invention.

Thus in allergic diseases such as asthma, or in the late phase reaction that characterizes allergic diseases, the proteins of the invention may function as agonists or antagonists, and the contribution to each may depend upon the specific concentration of each, the order in which they are administered, and the responsiveness of the basophils or mast cells in the vicinity. Therefore, combinations of one or more different proteins should also be useful in the methods of the invention. In addition, chimeric proteins including histamine-release inhibiting peptide fragments of two or more of the proteins, or other mediator-release inhibiting agents, of the invention may be used in this method.

Other Embodiments

Other embodiments are within the following claims. It should be understood that the examples and embodiments described herein are for illustrative purposes only, and that various modifications or changes in light thereof will be suggested to persons skilled in the art and are to be included within the scope of the appended claims.

What is claimed is:

1. A method of inhibiting histamine release from basophils or mast cells to treat an inflammatory disease associated with histamine release in a mammal, comprising administering to said mammal a systemic dosage of between 0.5 to 500 µg/kg of body weight of said mammal, a topical dosage of between 100 ng to 10 mg/surface area/day, or an inhalation dosage of 10 ng to 1 mg per inhalation of one or more proteins selected from the group consisting of MIP-1α, MIP-1β, CTAP-III, or IP-10.

2. The method of claim 1, wherein said mammal is a human.

3. The method of claim 1, wherein said protein is MIP-1α or MIP-1β.

4. The method of claim 1, wherein said protein is CTAP-III, or IP-10.

5. The method of claim 1, wherein said inflammatory disease is an allergic disease.

6. The method of claim 5, wherein said allergic disease is urticaria, angioedema, allergic conjunctivitis, atopic dermatitis, allergic contact dermatitis, a drug allergy, an insect sting allergy, or systemic anaphylaxis.

7. The method of claim 5, wherein said allergic disease is a respiratory allergic disease.

8. The method of claim 7, wherein said respiratory allergic disease is asthma.

9. The method of claim 1, wherein said protein is administered topically at a dosage of between 1 to 10 mg/m²/day of body surface area of said mammal.

10. The method of claim 1, wherein said protein is administered systemically at a dosage of between 20 to 200 µg/kg of body weight of said mammal.

11. The method of claim 1, wherein said protein is administered by inhalation at a dosage of between 100 ng to 100 µg per inhalation.

12. The method of claim 1, wherein said protein is administered systemically by intravenous, intraarterial, intramuscular, subcutaneous, or oral administration.

13. The method of claim 1, wherein said protein is administered topically by transdermal, or intranasal administration.

14. A method of inhibiting allergic disease in a mammal, comprising administering to said mammal a systemic dosage of between 0.5 to 500 µg/kg of body weight of said mammal, a topical dosage of between 100 ng to 10 mg/surface area/day, or an inhalation dosage of 10 ng to 1 mg per inhalation of one or more proteins selected from the group consisting of, MIP-1α, MIP-1β, CTAP-III, or IP-10.

15. The method of claim 14, wherein said mammal is a human.

16. The method of claim 14, wherein said allergic disease is a respiratory allergic disease.

17. The method of claim 16, wherein said respiratory allergic disease is asthma.

18. The method of claim 17, wherein said protein is administered by inhalation at a dosage of between 100 ng to 100 μg per inhalation.

* * * * *

UNITED STATES PATENT AND TRADEMARK OFFICE
CERTIFICATE OF CORRECTION

PATENT NO.  : 5,474,983

DATED       : December 12, 1995

INVENTOR(S) : Kuna et al.

It is certified that error appears in the above-identified patent and that said Letters Patent is hereby corrected as shown below:

Col. 1, line 9, "1526N" should be --P50 AI 16337-14--;
    line 56, "supernatant" should be --supernatants--.

Col. 2, line 17, after "upon" delete --"--.
    line 18, after "secreted" insert --"--.

Col. 3, line 15, "IP-10,and" should be --IP-10, and--.

Col. 4, line 18, "MIP-62" should be --MIP-1$\beta$--;
    "IP-10,or" should be --IP-10, or--.

Col. 6, line 6, "Lus" should be --Lys--;
    "Avg" should be --Arg--;
    line 8, "Alu" should be --Glu--;
    line 9, "Asa" should be --Asn--.

UNITED STATES PATENT AND TRADEMARK OFFICE
CERTIFICATE OF CORRECTION

PATENT NO.   : 5,474,983

DATED        : December 12, 1995

INVENTOR(S)  : Kuna et al.

It is certified that error appears in the above-identified patent and that said Letters Patent is hereby corrected as shown below:

Col. 7, line 16, after "NaCl, insert --, 0.1--;
    line 19, "$A_{280}nm$" should be --$A_{280nm}$--;
    line 33, "$MgCl_{12}$" should be --$MgCl_2$--.

Col. 8, line 12, after "4°C" insert a comma;
    line 55, "$10^{-1}M$" should be --$10^{-11}M$--.

Col. 9, line 43, "5X10hu - 11M" should be --$5X10^{-11}M$--.

Col. 10, in table III, in the title "HISTAKINE" should be --HISTAMINE--;
    in col. 1, line 10, "$5 \times 10^9 M$" should be --$5 \times 10^{-9}M$--;
    in col. 2, line 2, "41.3±6" should be --41.3±6§--.

Col. 11, lines 28-29, "$5x10-_9M$" should be --"$5x10^{-9}M$"--;

Col. 14, claim 1, line 27, after "proteins" insert a comma.

Col. 15, claim 14, line 2, after "proteins" insert a comma.

Signed and Sealed this

Thirtieth Day of September, 1997

Attest:

BRUCE LEHMAN

*Attesting Officer*          *Commissioner of Patents and Trademarks*